US011278058B2

(12) United States Patent
Atkins et al.

(10) Patent No.: US 11,278,058 B2
(45) Date of Patent: Mar. 22, 2022

(54) WICK FOR VAPORIZER DEVICE

(71) Applicant: JUUL Labs, Inc., San Francisco, CA (US)

(72) Inventors: Ariel Atkins, San Francisco, CA (US); Adam Bowen, San Mateo, CA (US); Esteban Leon Duque, Berkeley, CA (US)

(73) Assignee: JUUL LABS, INC., San Francisco, CA (US)

( * ) Notice: Subject to any disclaimer, the term of this patent is extended or adjusted under 35 U.S.C. 154(b) by 0 days.

(21) Appl. No.: 16/643,490

(22) PCT Filed: Aug. 28, 2018

(86) PCT No.: PCT/US2018/048368
§ 371 (c)(1),
(2) Date: Feb. 28, 2020

(87) PCT Pub. No.: WO2019/046315
PCT Pub. Date: Mar. 7, 2019

(65) Prior Publication Data
US 2020/0221771 A1  Jul. 16, 2020

Related U.S. Application Data

(60) Provisional application No. 62/721,512, filed on Aug. 22, 2018, provisional application No. 62/551,113, filed on Aug. 28, 2017.

(51) Int. Cl.
*A24F 3/00* (2006.01)
*A24F 17/00* (2006.01)
(Continued)

(52) U.S. Cl.
CPC ............... *A24F 40/44* (2020.01); *A24F 40/42* (2020.01); *A24F 40/485* (2020.01); *A24F 40/10* (2020.01); *A24F 40/46* (2020.01)

(58) Field of Classification Search
CPC ...................................................... A24F 40/44
See application file for complete search history.

(56) References Cited

U.S. PATENT DOCUMENTS

| 4,793,365 A | 12/1988 | Sensabaugh et al. |
| 4,990,939 A | 2/1991 | Sekiya et al. |

(Continued)

FOREIGN PATENT DOCUMENTS

| CA | 2846286 C | 8/2016 |
| CA | 3009050 C | 6/2020 |

(Continued)

*Primary Examiner* — Abdullah A Riyami
*Assistant Examiner* — Thang H Nguyen
(74) *Attorney, Agent, or Firm* — Mintz, Levin, Cohn, Ferris, Glovsky and Popeo, P.C.

(57) ABSTRACT

A vaporization device includes a wick with improved aerosol production properties relative to a traditional wick, for example one formed of silica fiberglass cord. According to some aspects, the wick is formed of discontinuous fibers that are not packed together and that have varying orientations, creating a plurality of voids, or spaces, between the various fibers and along the length of the wick. This design of voids along the length of the wick allows for rapid wick saturation and air exchange. Because of this, a user can take successive long puffs without noticing much difference in vapor production, as the liquid quickly (e.g., within seconds) replenishes in the wick.

20 Claims, 3 Drawing Sheets

(51) Int. Cl.
*A24F 25/00* (2006.01)
*A24F 40/44* (2020.01)
*A24F 40/485* (2020.01)
*A24F 40/42* (2020.01)
*A24F 40/10* (2020.01)
*A24F 40/46* (2020.01)

(56) References Cited

U.S. PATENT DOCUMENTS

| | | |
|---|---|---|
| 5,610,635 A | 3/1997 | Murray et al. |
| 5,994,025 A | 11/1999 | Iwasa et al. |
| 7,726,320 B2 | 6/2010 | Robinson et al. |
| 8,733,345 B2 | 5/2014 | Siller |
| 8,881,737 B2 | 11/2014 | Collett et al. |
| 9,004,073 B2 | 4/2015 | Tucker et al. |
| 9,155,336 B2 | 10/2015 | Liu |
| 9,277,770 B2 | 3/2016 | Depiano et al. |
| 9,282,772 B2 | 3/2016 | Tucker et al. |
| 9,289,014 B2 | 3/2016 | Tucker et al. |
| 9,326,547 B2 | 5/2016 | Tucker et al. |
| 9,439,456 B2 | 9/2016 | Liu |
| 9,474,306 B2 | 10/2016 | Tucker et al. |
| 9,510,623 B2 | 12/2016 | Tucker et al. |
| 9,554,597 B2 | 1/2017 | Liu |
| 9,609,893 B2 | 4/2017 | Novak et al. |
| 9,635,886 B2 | 5/2017 | Tu et al. |
| 9,648,908 B1 | 5/2017 | Rinehart et al. |
| 9,668,523 B2 | 6/2017 | Tucker et al. |
| 9,681,688 B1 | 6/2017 | Rinehart et al. |
| 9,723,876 B2 | 8/2017 | Cadieux et al. |
| 9,730,471 B2 | 8/2017 | Li et al. |
| 9,814,265 B2 | 11/2017 | Rinker et al. |
| 9,854,839 B2 | 1/2018 | Tucker et al. |
| 9,877,521 B1 | 1/2018 | Gillis |
| 9,999,250 B2 | 6/2018 | Minskoff et al. |
| 10,058,124 B2 | 8/2018 | Monsees et al. |
| 10,085,481 B2 | 10/2018 | Verleur et al. |
| 10,188,148 B2 | 1/2019 | Althorpe et al. |
| 10,279,934 B2 | 5/2019 | Christensen et al. |
| 10,357,060 B2 | 7/2019 | Rostami et al. |
| 10,368,580 B2 | 8/2019 | Rostami et al. |
| 10,369,302 B2 | 8/2019 | Suzuki et al. |
| 10,405,583 B2 | 9/2019 | Tucker et al. |
| 10,517,331 B2 | 12/2019 | Atkins et al. |
| 10,653,180 B2 | 5/2020 | Monsees et al. |
| 2005/0016550 A1 | 1/2005 | Katase |
| 2005/0034723 A1 | 2/2005 | Bennett et al. |
| 2005/0067503 A1 | 3/2005 | Katase |
| 2007/0079889 A1 | 4/2007 | Lindsay et al. |
| 2007/0215168 A1 | 9/2007 | Banerjee et al. |
| 2007/0295347 A1 | 12/2007 | Paine et al. |
| 2008/0038363 A1 | 2/2008 | Zaffaroni et al. |
| 2009/0324206 A1 | 12/2009 | Young et al. |
| 2010/0181387 A1 | 7/2010 | Zaffaroni et al. |
| 2010/0186757 A1 | 7/2010 | Crooks et al. |
| 2011/0041861 A1 | 2/2011 | Sebastian et al. |
| 2011/0108023 A1 | 5/2011 | McKinney et al. |
| 2011/0126831 A1 | 6/2011 | Fernandez Pernia |
| 2012/0009766 A1 | 1/2012 | Adam et al. |
| 2012/0199146 A1 | 8/2012 | Marangos |
| 2013/0087160 A1 | 4/2013 | Gherghe |
| 2014/0109898 A1 | 4/2014 | Li et al. |
| 2014/0109921 A1 | 4/2014 | Chen |
| 2014/0130817 A1 | 5/2014 | Li et al. |
| 2014/0209108 A1 | 7/2014 | Li et al. |
| 2014/0261487 A1 | 9/2014 | Chapman et al. |
| 2014/0261493 A1 | 9/2014 | Smith et al. |
| 2014/0311503 A1 | 10/2014 | Liu |
| 2014/0332022 A1 | 11/2014 | Li et al. |
| 2014/0356607 A1 | 12/2014 | Woodcock |
| 2014/0376895 A1 | 12/2014 | Han |
| 2015/0020830 A1 | 1/2015 | Koller |
| 2015/0027457 A1 | 1/2015 | Janardhan et al. |
| 2015/0059780 A1 | 3/2015 | Davis et al. |
| 2015/0090253 A1 | 4/2015 | Farrow |
| 2015/0157054 A1 | 6/2015 | Liu |
| 2015/0208731 A1 | 7/2015 | Malamud et al. |
| 2015/0245659 A1 | 9/2015 | DePiano et al. |
| 2015/0245669 A1 | 9/2015 | Cadieux et al. |
| 2015/0257447 A1 | 9/2015 | Sullivan |
| 2015/0335070 A1 | 11/2015 | Sears et al. |
| 2016/0007653 A1 | 1/2016 | Tu |
| 2016/0015082 A1 | 1/2016 | Liu |
| 2016/0021934 A1 | 1/2016 | Cadieux et al. |
| 2016/0044965 A1 | 2/2016 | Liu |
| 2016/0095357 A1 | 4/2016 | Burton |
| 2016/0109115 A1 | 4/2016 | Lipowicz |
| 2016/0128390 A1 | 5/2016 | Liu |
| 2016/0138795 A1 | 5/2016 | Meinhart et al. |
| 2016/0150827 A1 | 6/2016 | Liu |
| 2016/0157523 A1 | 6/2016 | Liu |
| 2016/0192708 A1 | 7/2016 | DeMeritt et al. |
| 2016/0255876 A1 | 9/2016 | Rostami |
| 2016/0255878 A1 | 9/2016 | Huang et al. |
| 2016/0286865 A1 | 10/2016 | King et al. |
| 2016/0345621 A1 | 12/2016 | Li et al. |
| 2016/0345632 A1 | 12/2016 | Lipowicz |
| 2016/0360792 A1 | 12/2016 | Liu et al. |
| 2016/0366725 A1 | 12/2016 | Tucker et al. |
| 2016/0374394 A1 | 12/2016 | Hawes et al. |
| 2016/0374399 A1 | 12/2016 | Monsees et al. |
| 2017/0006917 A1 | 1/2017 | Alvarez |
| 2017/0027227 A1 | 2/2017 | Lipowicz |
| 2017/0035110 A1 | 2/2017 | Keen |
| 2017/0071249 A1 | 3/2017 | Ampolini et al. |
| 2017/0108210 A1 | 4/2017 | Meinhart et al. |
| 2017/0127725 A1 | 5/2017 | Buchberger et al. |
| 2017/0150753 A1 | 6/2017 | Macko et al. |
| 2017/0162797 A1 | 6/2017 | Lee et al. |
| 2017/0188626 A1 | 7/2017 | Davis et al. |
| 2017/0188635 A1 | 7/2017 | Force et al. |
| 2017/0231286 A1 | 8/2017 | Borkovec et al. |
| 2017/0233114 A1* | 8/2017 | Christensen ............ B65B 3/003 141/2 |
| 2017/0251721 A1 | 9/2017 | Rostami et al. |
| 2017/0251722 A1 | 9/2017 | Kobal et al. |
| 2017/0251723 A1 | 9/2017 | Kobal et al. |
| 2017/0251727 A1 | 9/2017 | Nielsen |
| 2017/0258134 A1 | 9/2017 | Kane |
| 2017/0258137 A1 | 9/2017 | Smith et al. |
| 2017/0258138 A1 | 9/2017 | Rostami et al. |
| 2017/0258140 A1 | 9/2017 | Rostami et al. |
| 2017/0265524 A1 | 9/2017 | Cadieux et al. |
| 2017/0280769 A1 | 10/2017 | Li et al. |
| 2017/0280771 A1 | 10/2017 | Courbat et al. |
| 2017/0290370 A1 | 10/2017 | Garthaffner et al. |
| 2017/0295844 A1 | 10/2017 | Thevenaz et al. |
| 2017/0367407 A1 | 12/2017 | Althorpe et al. |
| 2018/0007966 A1 | 1/2018 | Li et al. |
| 2018/0022516 A1 | 1/2018 | Liu |
| 2018/0027878 A1 | 2/2018 | Dendy et al. |
| 2018/0077967 A1 | 3/2018 | Hatton et al. |
| 2018/0110940 A1 | 4/2018 | Suzuki et al. |
| 2018/0177240 A1 | 6/2018 | Duque et al. |
| 2018/0296777 A1 | 10/2018 | Terry et al. |
| 2018/0325183 A1 | 11/2018 | Huang et al. |
| 2019/0021400 A1* | 1/2019 | Fornarelli ................. A24F 7/00 |
| 2019/0046745 A1 | 2/2019 | Nettenstrom et al. |
| 2019/0099561 A1 | 4/2019 | Nettenstrom |
| 2019/0124982 A1 | 5/2019 | Atkins et al. |
| 2019/0166913 A1 | 6/2019 | Trzecieski |
| 2019/0200674 A1 | 7/2019 | Tucker et al. |
| 2019/0246693 A1 | 8/2019 | Nettenstrom et al. |
| 2019/0281896 A1* | 9/2019 | Chapman ................ A24F 40/44 |
| 2019/0373953 A1 | 12/2019 | Atkins et al. |
| 2019/0387797 A1 | 12/2019 | Christensen et al. |
| 2020/0000151 A1* | 1/2020 | Fraser .................... A24F 40/40 |
| 2020/0107585 A1 | 4/2020 | Atkins et al. |
| 2021/0329976 A1* | 10/2021 | Nelson .................... A24F 40/46 |

FOREIGN PATENT DOCUMENTS

| | | |
|---|---|---|
| CN | 103141944 A | 6/2013 |
| CN | 203748667 U | 8/2014 |

(56) References Cited

FOREIGN PATENT DOCUMENTS

| | | |
|---|---|---|
| EP | 2967154 B1 | 10/2018 |
| GB | 2504076 A | 1/2014 |
| KR | 20110006928 U | 7/2011 |
| KR | 20120008751 U | 12/2012 |
| KR | 101324667 B1 | 11/2013 |
| KR | 101369372 B1 | 3/2014 |
| KR | 101634882 B1 | 6/2016 |
| KR | 20180034451 A | 4/2018 |
| KR | 20180083424 A | 7/2018 |
| WO | WO-2004076289 A2 | 9/2004 |
| WO | WO-2010003480 A1 | 1/2010 |
| WO | WO-2014159982 A1 | 10/2014 |
| WO | WO-2015032093 A1 | 3/2015 |
| WO | WO-2016079151 A1 | 5/2016 |
| WO | WO-2016079155 A1 | 5/2016 |
| WO | WO-2016082103 A1 | 6/2016 |
| WO | WO-2016099276 A1 | 6/2016 |
| WO | WO-2016122417 A1 | 8/2016 |
| WO | WO-2016145611 A1 | 9/2016 |
| WO | WO-2016154897 A1 | 10/2016 |
| WO | WO-2016179376 A1 | 11/2016 |
| WO | WO-2016179828 A1 | 11/2016 |
| WO | WO-2016208760 A1 | 12/2016 |
| WO | WO-2017017970 A1 | 2/2017 |
| WO | WO-2017110713 A1 | 6/2017 |
| WO | WO-2017114389 A1 | 7/2017 |
| WO | WO-2017121253 A1 | 7/2017 |
| WO | WO-2017121546 A1 | 7/2017 |
| WO | WO-2017161725 A1 | 9/2017 |
| WO | WO-2017163044 A1 | 9/2017 |
| WO | WO-2017163051 A1 | 9/2017 |
| WO | WO-2017207443 A1 | 12/2017 |
| WO | WO-2018078546 A2 | 5/2018 |
| WO | WO-2018122380 A1 | 7/2018 |
| WO | WO-2018122978 A1 | 7/2018 |
| WO | WO-2018125934 A1 | 7/2018 |
| WO | WO-2018172765 A1 | 9/2018 |
| WO | WO-2019073010 A1 | 4/2019 |
| WO | WO-2020025644 A1 | 2/2020 |

\* cited by examiner

WICK FOR VAPORIZER DEVICE

CROSS REFERENCE TO RELATED APPLICATIONS

This application claims priority to U.S. provisional application No. 62/551,113, titled "WICK FOR VAPORIZER DEVICE," filed on Aug. 28, 2017, and U.S. provisional application No. 62/721,512, titled "WICK FOR VAPORIZER DEVICE," filed on Aug. 22, 2018, the contents of which are fully incorporated by reference.

BACKGROUND

Vaporizing devices, including electronic vaporizers or e-vaporizer devices, allow the delivery of vapor containing one or more active ingredients by inhalation of the vapor. Electronic vaporizer devices are gaining increasing popularity both for prescriptive medical use, in delivering medicaments, and for consumption of tobacco or other plant-based smokeable materials, including solid (e.g., loose-leaf) materials, solid/liquid (e.g., suspensions, liquid-coated) materials, wax extracts, and prefilled pods (e.g., cartridges, wrapped containers, and/or the like) of such materials. Electronic vaporizer devices in particular may be portable, self-contained, and/or convenient for use.

Electronic vaporizers may use an atomizer system that includes a wicking element with a resistive heating element, such as a coil wrapped around the wicking element or positioned within a hollowed wicking element.

Vaporizer devices can utilize a wick formed of a silica or cotton material. Silica wick material can be formed by bundling together fine, continuous filaments of silica glass into threads, which are then bundled together to form a cord or rope used as the wick. The cord may be specified by a nominal outer diameter, number of threads, and/or a TEX value indicating a linear density. TEX is, in accordance with implementations described here, a unit of weight used to measure the density of yarns, equal to 1 gram per 1000 meters.

Atomizer systems in which liquid is drawn into the wick from a reservoir are limited in that the liquid is drawn in longitudinally at end points of the silica cord (e.g., at end points of the continuous filaments of silica). This design suffers from a timing standpoint, as during use of a vaporizer device, liquid may not be replenished as quickly as desired for a user as the liquid evaporates from a heated region of the wick and more liquid needs to travel along the length of the wick for replenishment.

SUMMARY

Aspects of the current subject matter relate to a wick, for a vaporization device, formed of one or more materials, such as glass, cotton, and/or or the like, or a combination thereof. In particular, the wick can have a plurality of voids along its length for use in a vaporizer device.

In some implementations, a cartridge for a vaporization device can comprise a mouthpiece, a tank configured to hold a vaporizable material, a wick configured to draw the vaporizable material from the tank to a vaporization region, and a heating element disposed near the vaporization region. The wick can have a length and one more voids along the length. The heating element can be configured to heat the vaporizable material drawn from the tank by the wick.

In some related implementations, the heating element can at least partially encircle at least a portion of the wick, the wick can comprise a plurality of discontinuous glass filaments, the wick can comprise a heat-vaporizable coating, the heating element can be disposed between a pair of plates, the mouthpiece can be disposed at a first end of a body of the cartridge, and/or the heating element can be disposed at a second end of the body that is opposite the first end.

In other related implementations, the cartridge can further comprise an air inlet passage. The air inlet passage can be configured to direct a flow of air over the wick such that when the heating element is activated, the vaporizable material drawn by the wick into the vaporization region is evaporated into the flow of air. In some aspects, the wick and the heating element can be configured to cause aerosolization of the vaporizable material.

In other related implementations, the wick can comprise a glass wick. The glass wick can be characterized by a TEX value that is between 400 and 1000, between 500 and 900, between 600 and 800, between 600 and 700, between 640 and 680, and/or between 650 and 670. The glass wick can be characterized by a TEX value that is 660, approximately 660, or near 660.

In other related implementations, the wick can be characterized by at least a 10% volume of void spaces to the total volume of the wick or at least a 5% volume of void spaces to the total volume of the wick.

In other related implementations, the cartridge may not be present and the vaporization device may instead include the tank configured to hold the vaporizable material, the wick configured to draw the vaporizable material from the tank to the vaporization region, and/or the heating element disposed near the vaporization region.

In some implementations, a vaporization device can comprise a tank configured to hold a vaporizable material, a wick configured to draw the vaporizable material from the tank to a vaporization region, and/or a heating element disposed near the vaporization region. The wick can have a length and one or more fibers. The heating element can be configured to generate heat, a portion of the heat being transferred to the vaporizable material to aerosolize the vaporizable material.

In some related implementations, the wick can include an inner wick material and/or an outer jacket that at least partially surrounds the inner wick material. The inner wick material can comprise a glass material and/or the outer jacket can comprise a cotton material, a hemp material, another fibrous material, and/or the like. The inner wick material can be characterized by a TEX value that is between 400 and 1000, between 500 and 900, between 600 and 800, and/or between 600 and 700, between 640 and 680, and/or between 650 and 670. The inner wick material can be characterized by a TEX value that is 660, approximately 660, or near 660.

In other related implementations, the inner wick can be characterized by at least a 10% volume of void spaces to the total volume of the inner wick or at least a 5% volume of void spaces to the total volume of the inner wick.

In other related implementations, the heating element can at least partially encircle at least a portion of the wick, the inner wick material can comprise a plurality of discontinuous glass filaments, the wick can comprise a heat-vaporizable coating, and/or the heating element can be disposed between a pair of plates.

In other related implementations, the vaporization device can further comprise an air inlet passage. The air inlet passage can be configured to direct a flow of air over the wick such that when the heating element is activated, the vaporizable material drawn by the wick into the vaporization region is evaporated into the flow of air. In some aspects, the wick and the heating element can be configured to cause aerosolization of the vaporizable material.

In other related implementations, the vaporization device can comprise a cartridge comprising the tank configured to hold a vaporizable material, the wick configured to draw the vaporizable material from the tank to a vaporization region, and/or the heating element disposed near the vaporization region. In some aspects, a mouthpiece can be disposed at a first end of a body of the cartridge and/or the heating element can be disposed at a second end of the body that is opposite the first end.

In some implementations, a method of providing a vapor and/or aerosol for inhalation by a user can include drawing, through a wick, a vaporizable material from a tank of a vaporization device to a vaporization region, the wick having a plurality of voids along its length. The method can further include heating the vaporization region with a heating element disposed near the vaporization region to cause vaporization of the vaporizable material. The method can further include causing the vaporized vaporizable material to be entrained in a flow of air to a mouthpiece of the vaporization device. In some aspects, the vaporization device can include the vaporization device and/or cartridge described in any of the implementations described herein.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

Figure 1:
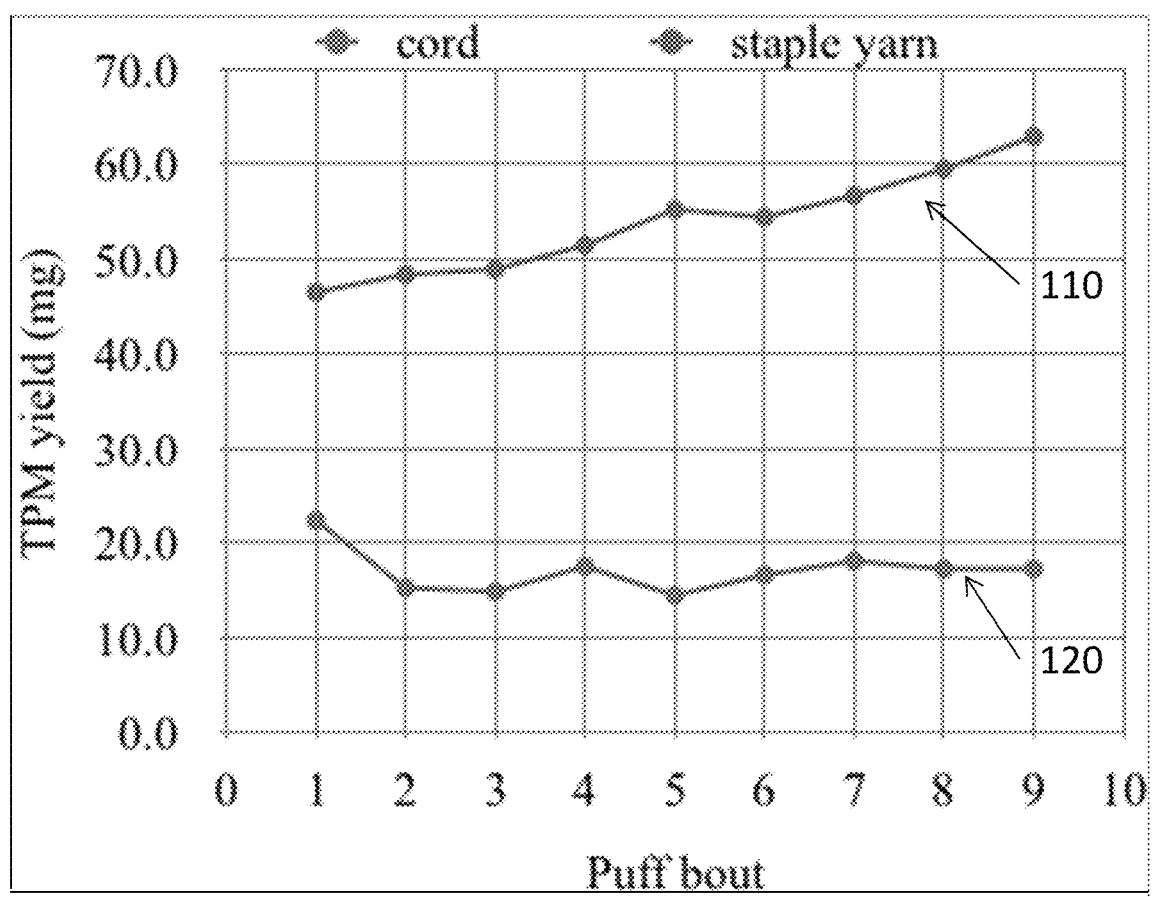
FIG. 1 illustrates, via a graph, experimental results comparing mass removal properties of a glass wick, consistent with implementations of the current subject matter, in a vaporizer device to that of a silica cord wick in a vaporizer device.

Implementations of the current subject matter include devices relating to vaporizing of one or more materials for inhalation by a user. The term "vaporizer" is used generically in the following description and refers to a vaporizer device. Examples of vaporizers consistent with implementations of the current subject matter include electronic vaporizers, electronic cigarettes, e-cigarettes, and/or the like. In general, such vaporizers can be portable and/or hand-held devices that heat a vaporizable material to provide an inhalable dose of the material.

Electronic vaporizers can use an atomizer system that includes a wicking element (or wick) with a resistive heating element such as a coil wrapped around the wicking element or positioned within a hollow wicking element. Other wick configurations are also possible, as discussed further below.

The wick serves at least two purposes: to draw liquid from a reservoir to the atomizer where it can be vaporized by the coil; and to allow air to enter the reservoir to replace the volume of liquid removed. When a user inhales on the vaporizer, the coil heater may be activated, and incoming may air pass over the saturated wick/coil assembly, stripping off vapor, which condenses and enters the user's lungs. During and/or after the puff, capillary action pulls more liquid into the wick and air returns to the reservoir through the wick.

A vaporizer consistent with implementations of the current subject matter can include a wick having a plurality of voids along its length. The wick according to some implementations of the current subject matter may be a glass wick formed of discontinuous glass fibers that are finite in length and/or spun together to form a yarn. In some aspects, the discontinuous glass fibers making up the wick are not packed together and have varying orientations, creating a plurality of voids, or spaces, between the various fibers and along the length of the wick. This design of voids along the length of the wick results in improved aerosol production properties relative to a traditional wick, for example one formed of silica fiberglass cord, by maintaining more liquid per unit volume in close proximity to the evaporation surface. During a puff, this liquid need only wick radially (or in a direction orthogonal to the evaporator surface). Between puffs, more time is available for this liquid to be replenished axially. Because of this, the mass density for a given puff can be higher than an equivalent design with a more conventional, corded wick.

A wick consistent with implementations of the current subject matter has increased liquid-carrying capacity, while also being thermally stable and having sufficient structural integrity for its use in vaporizer devices.

A wick consistent with implementations of the current subject matter may have a TEX value from between about 400 to about 1,000, preferably between about 600 to about 800. In some implementations, the wick has a TEX value of 660. Other TEX values may be used. A glass wick consistent with implementations of the current subject matter may be a Decofil C-Glass Staple Fiber Yarn, such as Decofil CD 11.5 660 L01P A1 or the like, which may be from another manufacturer. The wick may be formed of continuous or discontinuous C-Glass filaments, brought together to form a sliver, a yarn, and/or the like.

According to some aspects of the current subject matter, materials other than discontinuous glass fibers may be used to form a wick with voids along its length to allow for replenishment of liquid radially (or in a direction orthogonal to the evaporator surface) and axially along the wick. For example, a porous material, such as a ceramic material, having a plurality of voids or spaces along its length may be used as a suitable wicking material for the wick. Alternatively, other materials or fibers that are finite in length and that can be spun together to form a yarn, or other structure having voids along its length, may be used as a suitable wicking material. Such materials may be characterized by, for example, at least a 10% volume of void spaces to the total volume of the wick. According to additional aspects of the current subject matter, a suitable wicking material is characterized by at least a 5% volume of void spaces to the total volume of the wick.

The use of a wick having features consistent with implementations of the current subject matter in a vaporizer device produces unexpected results. This is because the wicking performance of a glass material is worse in terms of capillary pressure as compared to more traditional, more porous wick materials (e.g., silica or cotton). However, by utilizing a wick having features consistent with implementations of the current subject matter, the aerosol density produced by the atomizer is improved, intra-puff, which is a result of the atomizer layout. As liquid has to traverse a long distance longitudinally from the reservoir, replenishment can easily become the rate-limiting step for aerosol production, no matter the capillary pressure. Thus, by incorporating a wick having a plurality of voids along its length, as described herein, there is an increased amount of liquid near the evaporator surface at the beginning of a puff, resulting in improved aerosol density.

A glass wick having features consistent with implementations of the current subject matter was compared with a reference silica cord wick to demonstrate the mass removal properties of the glass wick. The glass wick used was the Decofil CD 11.5 660 L01P A1 with a TEX value of 660. The reference silica cord wick used had eight strands, a diameter of 1.5 mm, a TEX value of 1450, and a twist value of 120°. A smoking machine was used with three replicates of each configuration of a vaporizer device with a glass wick and a vaporizer device with a reference silica cord wick (e.g., six device and cartridge combinations total). A standardized puff profile of 100 cc puff volume, 3 s puff duration, and 30 s inter-puff interval was utilized. Puffs were taken in 10-puff bouts. An initial weight of each vaporizer device and cartridge was taken, and the weight was taken again following each bout. Results are shown in the graph 100 of FIG. 1, which illustrates average mass lost for each configuration (data 110 for the glass wick configuration, data 120 for the reference silica cord wick configuration), for each successive bout. As can be seen in the graph 100, the glass wick is able to better replenish its liquid carrying capacity between puffs when compared to the reference silica cord wick as more mass is removed in the glass wick after each puff bout.

In some implementations, a wick can be formed of a combination of glass and another natural fibrous material, such as cotton, hemp, or the like. In some implementations, the wick can include an inner wick material and at least one outer jacket. In some exemplary implementations, the wick can include two or more outer jackets.

The inner wick material can be formed as a continuous or discontinuous thread, yarn or another strand configuration. The outer jacket can have a series of interlocking loops of material, or can be formed of a combination of solid tube-like material and/or porous tube or matrix of cross-stitched material. For instance, the inner wick material can be formed of glass, which can be continuous or discontinuous, and which inner wick material can be formed of one or more strands wound or provided together. In some implementations, inner wick material can include a glass wick having features consistent with implementations described herein. The outer jacket can be of a different material from the inner wick material and/or include a fibrous material, such as cotton, hemp, and/or the like. The outer jacket can be formed as a continuous sheath, can be formed as a matrix of cross-strands (e.g., knitted and/or the like), or any other formation.

In other implementations, the wick can include an inner wick material of a fibrous material, such as cotton, where the fibrous material can be continuous, such as a yarn or weave of one or more strands, or discontinuous, with one or more gaps along its length or along the length of one or more strands that make up the inner wick material. The wick can include an outer jacket made of glass or other rigid or semi-rigid, brittle yet porous material. such as glass.

In yet other implementations, in a configuration having an inner wick material and at least one outer jacket, either the inner wick material or at least one outer jacket can include detents, apertures, holes, separations, or the like, and which can be microscopic in size. Each of the inner wick material or the outer jacket can be embedded with additional materials to improve wicking and holding of a fluid to be vaporized.

Figure 2:
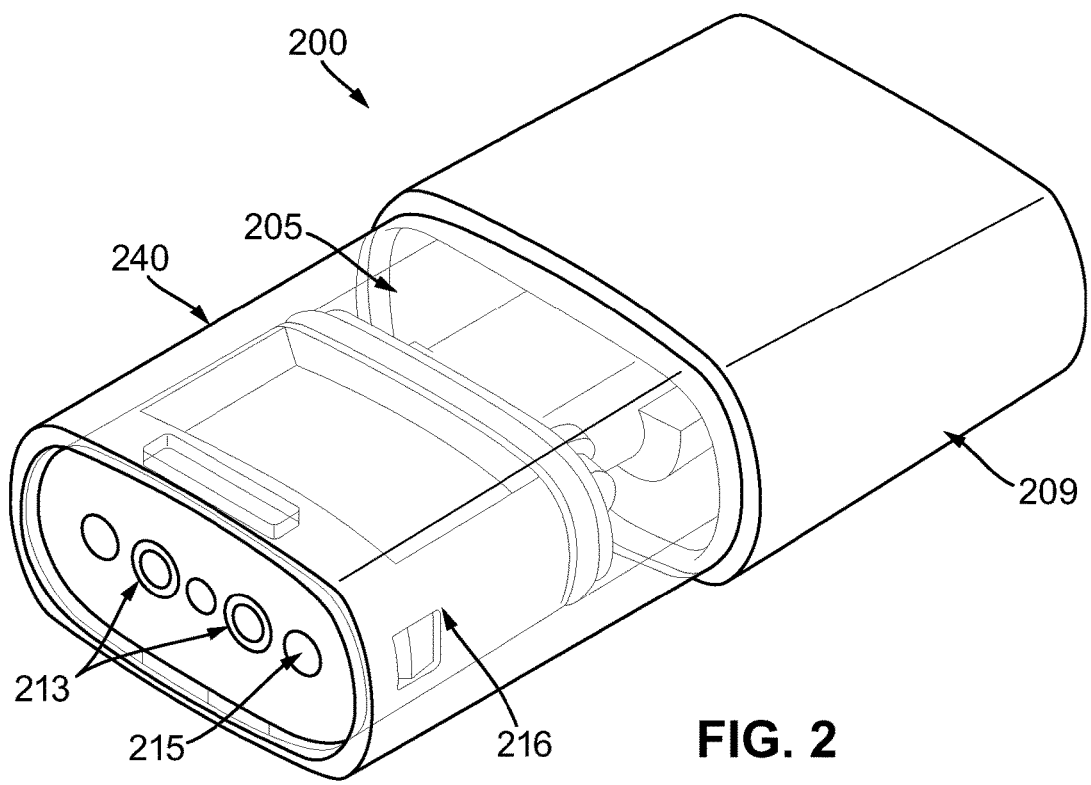
FIG. 2 illustrates, via a perspective view, a cartridge in which a wick consistent with implementations of the current subject matter may be incorporated.
Figure 3:
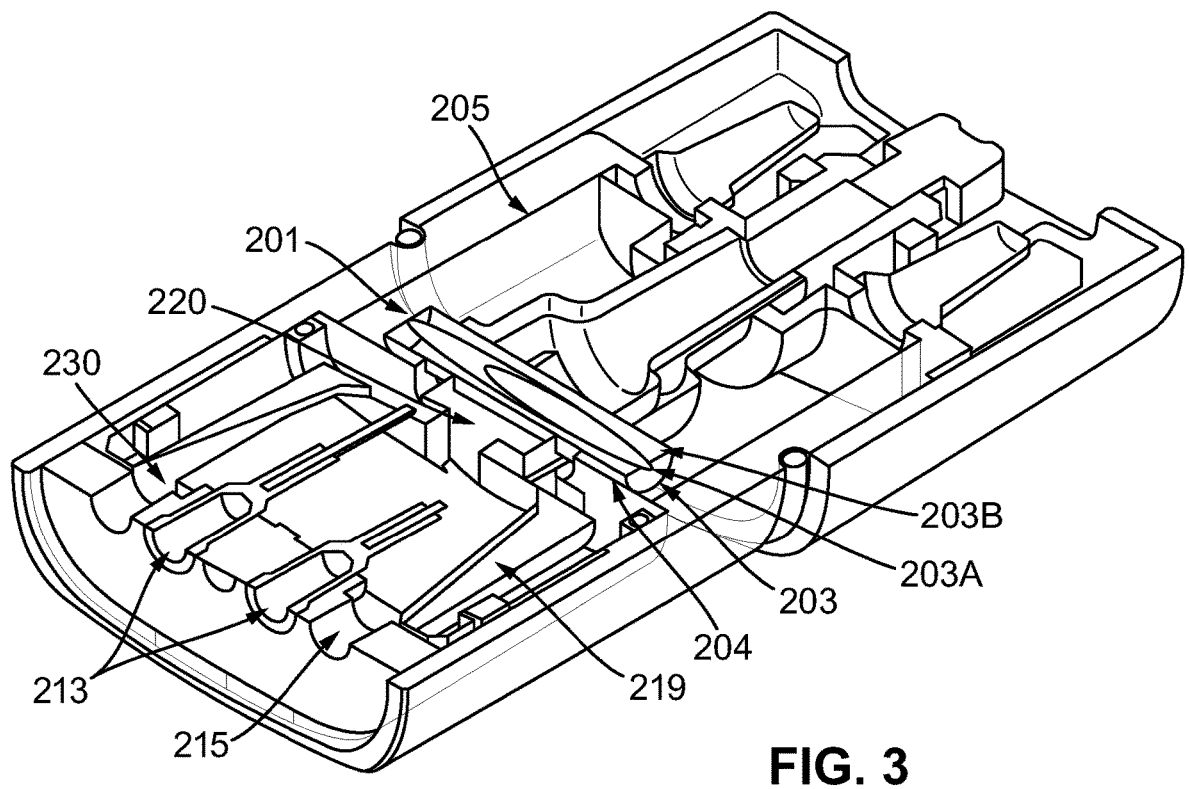
FIG. 3 illustrates, via a cross-sectional view, the cartridge of FIG. 2, showing the wick and internal resistive heating components.

FIGS. 2 and 3 illustrate an example of a cartridge 200 that may include or be adapted to include a wick consistent with implementations of the current subject matter. The wick 203 can include an inner wick material 203A and at least one outer jacket 203B. The cartridge can further comprise an air inlet passage 230. The air inlet passage 230 can be configured to direct a flow of air over the wick 203 such that when the heating element 204 is activated, the vaporizable material drawn by the wick 203 into the vaporization region 220 is evaporated into the flow of air. The cartridge 200 may be used with a vaporizer body (not shown) having a battery and control circuitry, together configured to generate an inhalable vapor by heating a vaporizable material before and/or as it enters a wick from which it can be vaporized.

In the example configuration shown in FIGS. 2 and 3, the cartridge 200 includes a tank (or reservoir) 205 for holding a vaporizable material (such as an oil or some other fluid or liquid), a proximal mouthpiece 209, a set of pin connectors 213 at the distal end, and openings 215 into an overflow leak chamber 216 (which may include one or more absorbent pads 219 for soaking up leakage of the vaporizable material as shown in FIG. 3), as well as a wick 203 consistent with implementations of the current subject matter. The wick 203 may be wrapped with a resistive heating element (coil 204), as shown in FIG. 3, which is connected by plates 201 to pin inputs. A heater may include the wick 203 extending between plates 201 and the heating element 204 in contact with both the plates 201 and the wick 203.

Air may be drawn in from the bottom or base of the cartridge 200, pulled over and around the heating element 204. An air path through the cartridge 200 passes through the tank 205. A heating chamber, holding the wick 203 and heating element 204, may be an internal chamber (e.g., surrounded by the tank) through which the airflow passes. The wick 203 may be suspended between a pair of heater contacts positioned in the heating chamber.

The wick 203 draws vaporizable material from the tank 205, from both ends of the wick 203 and radially along the length of the wick 203 due to the plurality of voids within the wick 203. When a user puffs on the cartridge 200, air flows into an inlet. Simultaneously, the heating element 204 may be activated, e.g., by a pressure sensor, pushbutton, motion sensor, flow sensor, or other approach capable of detecting that a user is taking a puff or otherwise inhaling through a flow path of the vaporizer device. When the heating element 204 is activated, the coil may have a temperature increase as a result of current flowing through the coil to generate heat. The heat is transferred to at least a portion of the vaporizable material in the tank 205 through conductive, convective, and/or radiative heat transfer such that at least a portion of the vaporizable material vaporizes. The incoming air into the vaporizer device flows over the heated wick/coil, stripping away the vaporized vaporizable material, where it is condensed and exits as an aerosol via the mouthpiece 209 to a user.

A wick 203 consistent with implementations of the current subject matter can provide a capillary pathway, for vaporizable material within the tank 205, through and into the wick 203. The capillary pathway is generally large enough to permit wicking to replace vaporized liquid transferred from the tank 205 by capillary action (wicking) during use of the vaporizer device, but may be small enough to prevent leakage of the vaporizable fluid material out of the cartridge 200 during normal operation, including when applying pressure to (e.g., squeezing) the cartridge 200. An external portion of the wick 203 may include a wick housing. The wick housing and/or wick 203 may be treated to prevent leakage. For example, the wick 203 and/or wick housing may be coated after filling to prevent leakage and/or evaporation through the wick 203 until activated by connecting to a vaporizer body and/or applying current through electrical contacts (e.g., operation in a vaporizer device), or otherwise using the cartridge 200. Any appropriate coating may be used, including a heat-vaporizable coating (e.g., a wax or other material) or the like.

A wick consistent with implementations of the current subject matter may have an orientation other than that shown in the exemplary cartridge illustrations of FIGS. 2 and 3. For example, the wick 203 shown in FIG. 3 extends horizontally between two side portions of the cartridge 200. However, the wick is not limited to this orientation and may, for example, extend internally along a length of the body 240 of the cartridge 200 with the heating element at one end of the wick. Other orientations and configurations are also possible.

Although the example described herein with respect to FIGS. 2 and 3 is directed to a vaporizer that utilizes a removable cartridge, a wick consistent with implementations of the current subject matter is not limited to such a device configuration. For example, a wick may be incorporated as part of a vaporizer device that includes a reservoir in which the wick and the heating element are included or in contact with.

Figure 4:
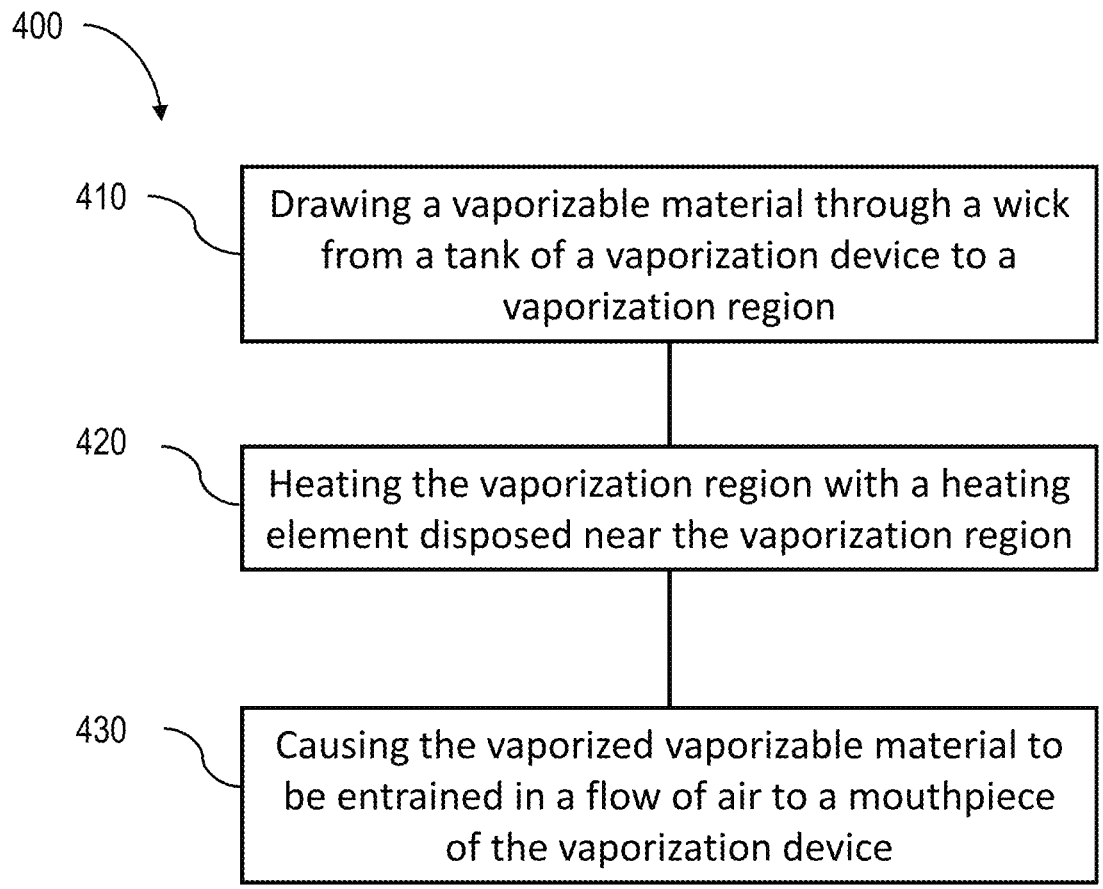
FIG. 4 shows a process flow chart illustrating features of a method of drawing a vaporizable material and causing vaporization of the vaporizable material in a vaporization device consistent with implementations of the current subject matter.

With reference to FIG. 4, a process flow chart 400 illustrates features of a method, which may optionally include some or all of the following. At 410, a vaporizable material is drawn, through a wick, from a tank of a vaporization device to a vaporization region. At 420, the vaporization region is heated with a heating element disposed near the vaporization region. The heating causes vaporization of the vaporizable material in the vaporization region. At 430, the vaporized vaporizable material is entrained in a flow of air to a mouthpiece of the vaporization device.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A cartridge for a vaporization device, the cartridge comprising:
   a mouthpiece;
   a tank configured to hold a vaporizable material;
   a wick configured to draw the vaporizable material from the tank to a vaporization region, the wick having a length and being formed from a plurality of discontinuous glass filaments creating one or more voids along the length, wherein the wick comprises a glass wick characterized by a TEX value of between 400 and 1000; and
   a heating element disposed near the vaporization region and configured to heat the vaporizable material drawn from the tank by the wick.

2. The cartridge of claim 1, wherein the heating element at least partially encircles at least a portion of the wick.

3. The cartridge of claim 1, further comprising an air inlet passage.

4. The cartridge of claim 3, wherein the air inlet passage is configured to direct a flow of air over the wick such that when the heating element is activated, the vaporizable material drawn by the wick into the vaporization region is evaporated into the flow of air.

5. The cartridge of claim 4, wherein the wick and the heating element are configured to cause aerosolization of the vaporizable material.

6. The cartridge of claim 1, wherein the plurality of discontinuous glass filaments are of varying orientations.

7. The cartridge of claim 6, wherein the plurality of discontinuous glass filaments are not packed together.

8. The cartridge of claim 1, wherein the glass wick is characterized by the TEX value of 660.

9. The cartridge of claim 1, wherein the wick is characterized by at least a 5% volume of void space to a total volume of the wick.

10. The cartridge of claim 1, wherein the wick comprises a heat-vaporizable coating.

11. The cartridge of claim 1, wherein the heating element is disposed between a pair of plates.

12. The cartridge of claim 1, wherein the mouthpiece is disposed at a first end of a body of the cartridge and the heating element is disposed at a second end of the body, opposite the first end.

13. A vaporization device comprising:
    a tank configured to hold a vaporizable material;
    a wick configured to draw the vaporizable material from the tank to a vaporization region, the wick having a length and being formed of one or more discontinuous glass fibers, wherein the wick comprises a glass wick characterized by a TEX value of between 400 and 1000; and
    a heating element disposed near the vaporization region, the heating element configured to generate heat, a portion of the heat being transferred to the vaporizable material to aerosolize the vaporizable material.

14. The vaporization device in accordance with claim 13, wherein the wick includes an inner wick material and an outer jacket that at least partially surrounds the inner wick material.

15. A method comprising:
    drawing, through a wick, a vaporizable material from a tank of a vaporization device to a vaporization region, the wick being formed from a plurality of discontinuous glass filaments creating a plurality of voids along its length, wherein the wick comprises a glass wick characterized by a TEX value of between 400 and 1000;
    heating the vaporization region with a heating element disposed near the vaporization region to cause vaporization of the vaporizable material; and causing the vaporized vaporizable material to be entrained in a flow of air to a mouthpiece of the vaporization device.

16. The cartridge of claim 14, wherein the outer jacket includes a fibrous material or glass.

17. The cartridge of claim 1, wherein the wick includes an inner wick material and an outer jacket that at least partially surrounds the inner wick material.

18. The cartridge of claim 17, wherein the outer jacket includes a fibrous material or glass.

19. The cartridge of claim 18, wherein the fibrous material is cotton or hemp.

20. The cartridge of claim 17, wherein the outer jacket can be formed as a continuous sheath or a matrix of cross-strands.

* * * * *

UNITED STATES PATENT AND TRADEMARK OFFICE
CERTIFICATE OF CORRECTION

| | |
|---|---|
| PATENT NO. | : 11,278,058 B2 |
| APPLICATION NO. | : 16/643490 |
| DATED | : March 22, 2022 |
| INVENTOR(S) | : Ariel Atkins et al. |

It is certified that error appears in the above-identified patent and that said Letters Patent is hereby corrected as shown below:

In the Claims

At Column 11, Claim 16, Line number 4 delete the words "cartridge of claim 14" and insert --vaporization device in accordance with claim 14--

Signed and Sealed this
Twenty-fourth Day of May, 2022

Katherine Kelly Vidal
*Director of the United States Patent and Trademark Office*